United States Patent [19]

Merrill

[11] Patent Number: 5,171,264
[45] Date of Patent: Dec. 15, 1992

[54] IMMOBILIZED POLYETHYLENE OXIDE STAR MOLECULES FOR BIOAPPLICATIONS

[75] Inventor: Edward W. Merrill, Belmont, Mass.

[73] Assignee: Massachusetts Institute of Technology, Cambridge, Mass.

[21] Appl. No.: 486,153

[22] Filed: Feb. 28, 1990

[51] Int. Cl.$^5$ .............................................. A61M 1/10
[52] U.S. Cl. ......................................... 623/3; 427/2;
427/337; 427/352; 427/533; 436/512; 436/518;
436/547; 436/828; 435/975; 623/1; 623/2;
606/194; 609/96
[58] Field of Search ...................... 427/2, 35, 352, 337;
436/547, DIG. 828, 512, 518; 435/975;
623/901, 1, 2, 3; 606/194; 604/96

[56] References Cited

U.S. PATENT DOCUMENTS

| | | | |
|---|---|---|---|
| 3,951,931 | 4/1976 | Burchard et al. | 525/389 |
| 4,280,923 | 7/1981 | Small et al. | 252/323 |
| 4,426,495 | 1/1984 | Vitus et al. | 525/92 |
| 4,452,892 | 6/1984 | Rosevear | 435/176 |
| 4,687,814 | 8/1987 | Chaumont et al. | 525/242 |
| 4,713,249 | 12/1987 | Schröder | 424/1.1 |
| 4,751,282 | 6/1988 | Takeo et al. | 528/312 |
| 4,794,144 | 12/1988 | Spinelli | 525/284 |
| 4,840,851 | 6/1989 | Golander et al. | 428/523 |
| 4,847,328 | 7/1989 | Hutchins et al. | 525/286 |
| 4,863,611 | 9/1989 | Bernstein et al. | 210/196 |
| 4,950,709 | 8/1990 | Schlueter et al. | 524/762 |

FOREIGN PATENT DOCUMENTS 0068509 1/1983 European Pat. Off. .
0263184 4/1988 European Pat. Off. .
0332261 9/1989 European Pat. Off. .

OTHER PUBLICATIONS

Rempp, R. & P. Lutz, Abstracts of the Papers of the American Chemical Society 196: 27–Poly (1988).
Rempp, P. et al., Advances in Polymer Science 86:145–173 (1988).
Taromi, F. A. and P. Rempp, Makromol. Chem. 190:1791–1798 (1989).
Gnanou, Y. et al., Makromol. Chem. 189:2885–2892 (1988).
Lutz, P. and P. Rempp, Makromol. Chem. 189:1051–1060 (1988).
Remp, P. et al., American Chemical Society, Polymer Division Symposium, Boston, MA Apr. 1990.
Merrill, E. W. et al., The 16th Annual Meeting of the Society for Biomaterials, Charleston, SC, May 20–23, 1990.
Tay, S. W. et al., Biomaterials 10:11–15 (1989).

Primary Examiner—Shrive Beck
Assistant Examiner—Diana L. Dudash
Attorney, Agent, or Firm—Hamilton, Brook, Smith & Reynolds

[57] ABSTRACT

This invention pertains to a method for immobilizing polyethylene oxide (PEO) star molecules in the form of hydrogels. The PEO star molecules are biocompatible and demonstrate non-thrombogenic properties. As such, the PEO star molecules have numerous uses for biomedical applications. The hydrogels contain a high percentage of terminal hydroxyl groups for attachment of affinity ligands and can be used for separating and purifying therapeutic proteins.

16 Claims, 4 Drawing Sheets

SUPPORT SURFACE

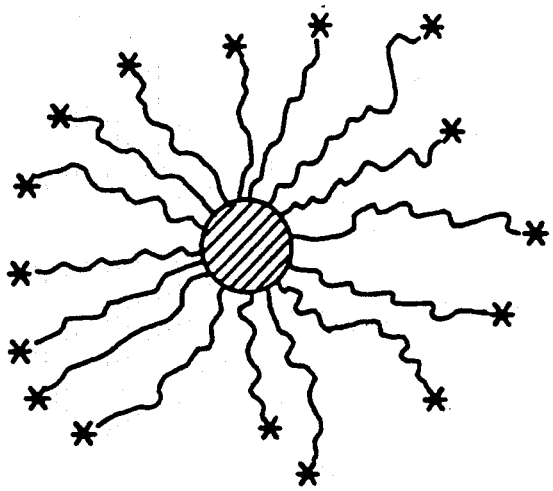
FIG. IA
LEGEND FOR FIG. IA & IB
◯ = CROSS-LINKED DIVINYL BENZENE CORE
∿∿ = PEO CHAIN
✻ = HYDROXYL GROUP
— = PST CHAIN
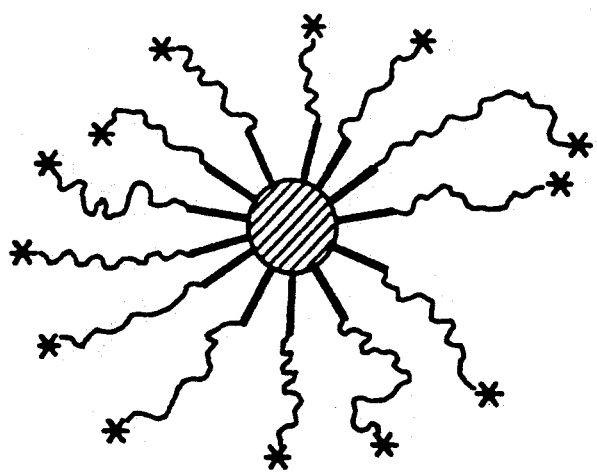
FIG. IB

⊘ = DVB CORE

✷ = HYDROXYL END

▲ = CROSS-LINK

\* = TRESYLATED HYDROXYL

▨ = ATTACHMENT TO AMINO GROUP ON SUPPORT SURFACE

IMMOBILIZED POLYETHYLENE OXIDE STAR MOLECULES FOR BIOAPPLICATIONS

BACKGROUND OF THE INVENTION

Polyethylene oxide (PEO) is an important biomaterial because it is non-thrombogenic, i.e., it does not adsorb proteins of the intrinsic clotting system nor of the platelet membrane. However, when PEO is combined with other molecules at the surface, thrombogenicity may be enhanced. Okkema, A. Z., *J. Biomat. Sci.* 1:43-62 (1989). Thus, it is essential that no other molecular entity besides PEO be accessible to proteins. It has been widely studied as a blood-contacting biomaterial in various forms: in segmented polyurethane, in block copolymers with styrene or siloxane blocks, end-linked into junctions through isocyanate reactions, as side-chains on acrylate polymers and as hydrogels cross-linked from PEO solutions.

PEO is naturally soluble in water and certain organic solvents. Therefore, in order to render PEO insoluble it must be crosslinked, or end-linked to a support. The manner in which this is accomplished often affects physical and chemical properties of PEO.

Chemical crosslinking of PEO can be employed but the chemical crosslinking agent (e.g., a polyglycidoxypropyl siloxane) may be incorporated into the PEO. This can cause adverse biopolymer reactions, including non-specific binding of proteins and platelet adhesion.

Physically crosslinked PEO produced from polyethylene oxide-polystyrene multiblock polymers or from polyether-urethanes suffers from the presence of the non-PEO material at the surface. Adverse biological reactions caused by the non-PEO material can be avoided if the molecular weight of the PEO is made higher than about 5000. However, such material tends to swell excessively in water and is fragile.

End-linking PEO to supports by various means, so as to leave an available hydroxyl group for attachment of an affinity ligand, for example, is not easily carried out if the molecular weight of the PEO is more than about 1000. Furthermore, complete coverage of a surface by end-linking PEO is very difficult, unless the molecular weight is relatively high (several thousand).

Various forms of PEO have also been widely used as a molecular leash for affinity ligands and enzymes. Golander, C. G. et al., *Int. Chem. Congress of Pacific Basin Societies*, Abstract No. 253, Honolulu, Hi., Dec. 17-22, 1989; Harris J. M., *J. Macromolecular Sci.* C25:325-373 (1985); Holmberg, K., *Int. Chem. Congress of Pacific Basin Societies*, Abstract No. 255, Honolulu, Hi., Dec. 17-22, 1989. Typically, PEO has terminal hydroxyl groups which can be activated for attachment to biopolymers. Most processes for forming PEO biomaterials, however, reduce the hydroxyl content to very low values or zero. In order to produce a crosslinked PEO having a significant concentration of terminal hydroxyls, low molecular weight PEO (2,000 to 10,000) are required but often result in fragile materials. Alternatively, using short PEO side chains on macrometers like polyethylene glycol methacrylate may result in exposure of the methacrylate residues at the surface.

Thus, a need exists for a method of immobilizing PEO to a support surface without detracting from its physical properties and biological compatability. In addition, it would be desirable to provide a material having a high concentration of hydroxyl groups for attachment to biopolymers.

SUMMARY OF THE INVENTION

This invention pertains to a method for covalently immobilizing polyethylene oxide star molecules onto a support surface and to hydrogels produced by the method. The PEO star molecules are immobilized in the form of hydrogels using radiation or hydroxyl group activation. The resulting PEO hydrogels have a high concentration of terminal hydroxyl groups which are available for attachment to biospecific affinity ligands or to the support surface itself. As such, the immobilized PEO star molecules can be used as a tool for separating and purifying biological molecules, while greatly reducing or eliminating non-specific binding.

The PEO star molecule hydrogels also have non-thrombogenic properties which make them suitable for applications in which blood contact is required. They are highly biocompatible and have excellent mechanical durability for numerous biomedical applications, including intravenous catheters and implantable vascular prostheses.

BRIEF DESCRIPTION OF THE DRAWINGS

FIG. 1a shows a Type I PEO star molecule having a divinyl benzene (DVB) core and PEO chains attached thereto.

FIG. 1b shows a Type II PEO star molecule having a DVB core and PEO chains attached thereto by polystyrene (PS) chains.

DETAILED DESCRIPTION OF THE INVENTION

Figure 2:
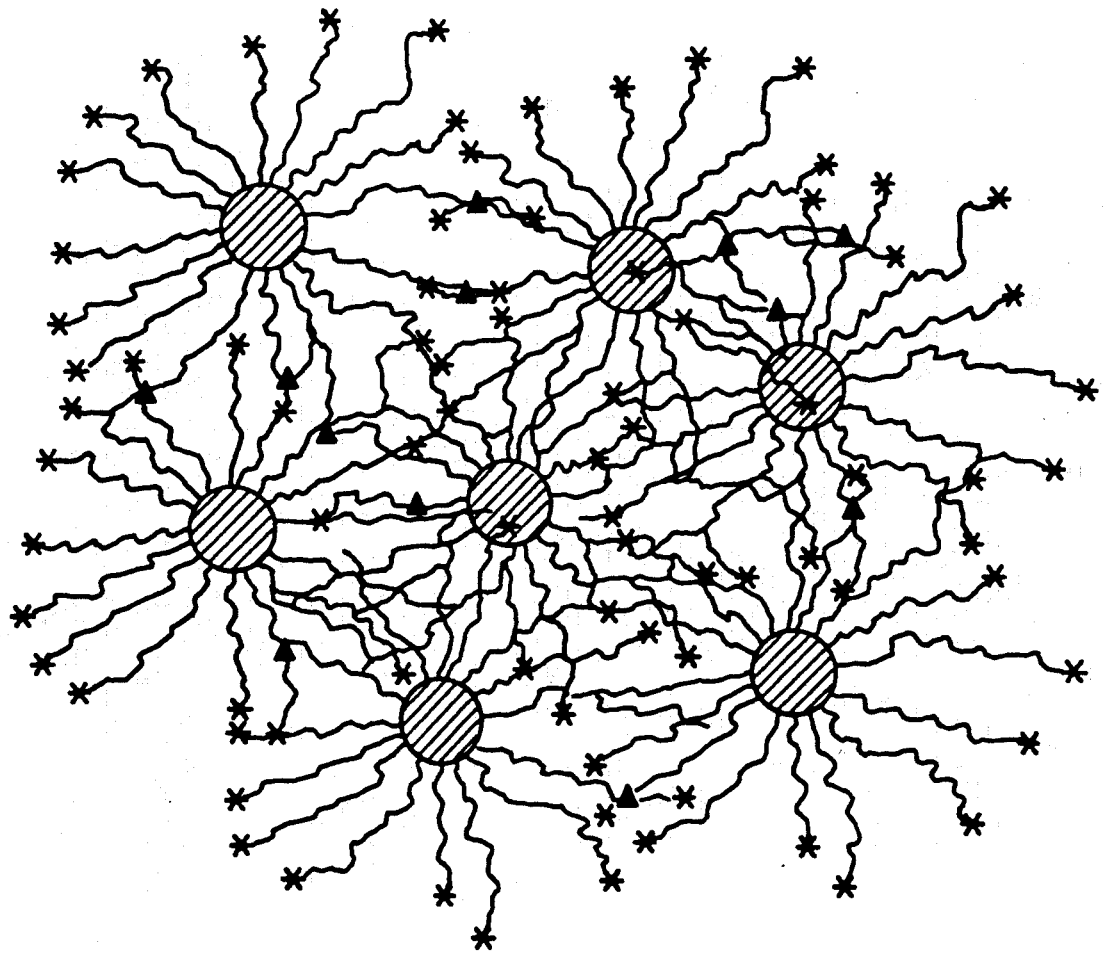
FIG. 2 shows overlapping PEO star molecules (Type I) which are crosslinked to each other by electron irradiation.

Polyethylene oxide star macromolecules have been previously described by Lutz, P. and P. Rempp, *Makromol. Chemie* 189:1051 (1988) and Gnanou, Y. et al., *Makromol. Chemie* 189:2893-2897 (1988), the teachings of which are incorporated by reference herein. The star molecules are synthesized by anionic polymerization from divinyl benzene (DVB), ethylene oxide and optionally styrene. They have a core of divinyl benzene (typically on the order of about 50 angstroms) from which a predetermined number of polyethylene oxide chains or "arms" are grown. The cores however can be of polymeric material other than divinyl benzene. The length of each PEO chain corresponds to its molecular weight and typically range from about 1,000 to about 10,000. Preferably, each star molecule will have from about 6 to about 50 arms. Two variations of PEO star molecules are shown in FIGS. 1A and 1B and are described herein as Type I and Type II, respectively. Type I star molecules contain a plurality of hydroxyl-terminated PEO chains (hydrophilic) that are attached to a hydrophobic DVB core by non-hydrolyzable carbon-carbon bonds. Type II PEO star molecules are of similar composition except that the PEO chains are attached to the DVB core via hydrophobic polystyrene (PS) chains.

The concentration of hydroxy-termini on the PEO arms can be determined in advance by selection of the gross concentration of star molecules and the number of arms carried by the molecule. For example, a star molecule of 100,000 molecular weight with 20 PEO arms has 20 hydroxyls. To obtain comparable hydroxyl concentrations with linear PEO polymers, the molecular weight would have to be lowered to 10,000. However, hydrogels made of cross-linked linear PEO of comparable molecular weights (MW 10,000) are very fragile.

The PEO star molecules can be immobilized or grafted onto a support surface of any geometry (e.g., particles, porous plastic cones, thin plastic film, biomedical device) using ionizing radiation. According to the method, PEO star molecules are dissolved or suspended in an aqueous solution (preferably water) in a concentration sufficient to provide enough star molecules to cover the support surface to desired thickness. Typically, a sufficient concentration will be around 5 to 15 wt/vol %. Type I star molecules form optically clear homogeneous solutions in water, while Type II star molecules form faintly turbid to opaque suspensions, due to the presence of polystyrene. The resulting solution is then deposited onto the support surface, such as by spreading, rotating the support or centrifugation.

The star molecules are then crosslinked together by exposing them to electron beam radiation which results in the formation of a hydrogel network. The term "hydrogel" refers to a broad class of polymeric materials which are swollen extensively in water but which do not dissolve in water. Typically, the solution is exposed to electron radiation in the range of from about 1 to about 6 megarads, most preferably 4 megarads. Gamma radiation can be used as the radiation source but may result in the degradation of the star molecules. Crosslinking occurs randomly between segments of the PEO arms, thus allowing the terminal hydroxyl groups to remain available for subsequent activation, such as coupling affinity ligands to the PEO arms.

FIG. 2 shows several Type I PEO star molecules crosslinked together by electron radiation. The resulting hydrogel layers are of variable thickness but are typically on the order of magnitude of $>1$ $\mu$M. The thickness of the hydrogel layer can be regulated by various techniques, such as doctor-blade spreading on a support web or centrifugal casting in tubes.

An advantage of electron radiation crosslinking is that the crosslinking reaction proceeds very rapidly, at a rate of approximately 1 foot/sec. in the case of web coating. The reaction proceeds by free-radical coupling to produce a pure product. As such, the crosslinking reaction does not alter the chemical composition of the star molecules. Other known cross-linking techniques tend to introduce chemical components which may subsequently affect is biocompatibility. Further, the hydrogel network has a surface for contacting biological materials (e.g. blood) which is essentially PEO chains. As such, the DVB and PS components are inaccessible or not recognizable to these biological molecules.

The resulting hydrogels have significantly greater mechanical strength than hydrogels formed from ordinary linear PEO having the same range of molecular weight as the star (i.e., 100,000 to 300,000). A gel made from 10 wt. % of 100,000 molecular weight linear PEO under identical dosage would have 2 to 10 times lower tensile strength than the network formed from star molecules, and would have only 1/10th the number of hydroxyl groups per unit area of surface. The concentrations of hydroxyl ends obtained by stars would translate to linear polyethylene oxide of around 5,000 mol. wt. or less. Such low molecular weight polymers cannot be crosslinked at all, or form gels of low strength with considerable soluble fraction.

In another embodiment, the star molecules can be covalently immobilized to a support surface by tresylation of the terminal hydroxyl groups. The support surface and star molecules are each pretreated prior to immobilization. As such, the support surface should contain active functional groups for immobilizing tresylated star molecules thereto, such as amino and/or thiol groups. Likewise, the star molecules should be tresylated in an appropriate solvent at pH 10 or above, prior to contacting with the support surface. Tresylation is particularly convenient since the PEO is solvated by media appropriate to tresyl chloride (e.g., dichloromethane, chloroform). This method results in a monolayer coating of the hydrogel over the support surface.

According to this method, an organic solution comprising PEO star molecules is exposed to tresyl chloride, under conditions such as to fix the tresyl groups to hydroxy-termini on the star molecules. The resulting tresylated PEO star molecules are then transferred from the organic solvent to an aqueous solution. The pH of the aqueous solution is then adjusted to about 10 or above, so as to favor reaction with amino and/or thiol groups on the support surface. The pH-adjusted solution is contacted with a pretreated surface support that contains amino and/or thiol groups, under conditions whereby the star molecules become covalently bound in a dense layer to the support surface.

Figure 3:
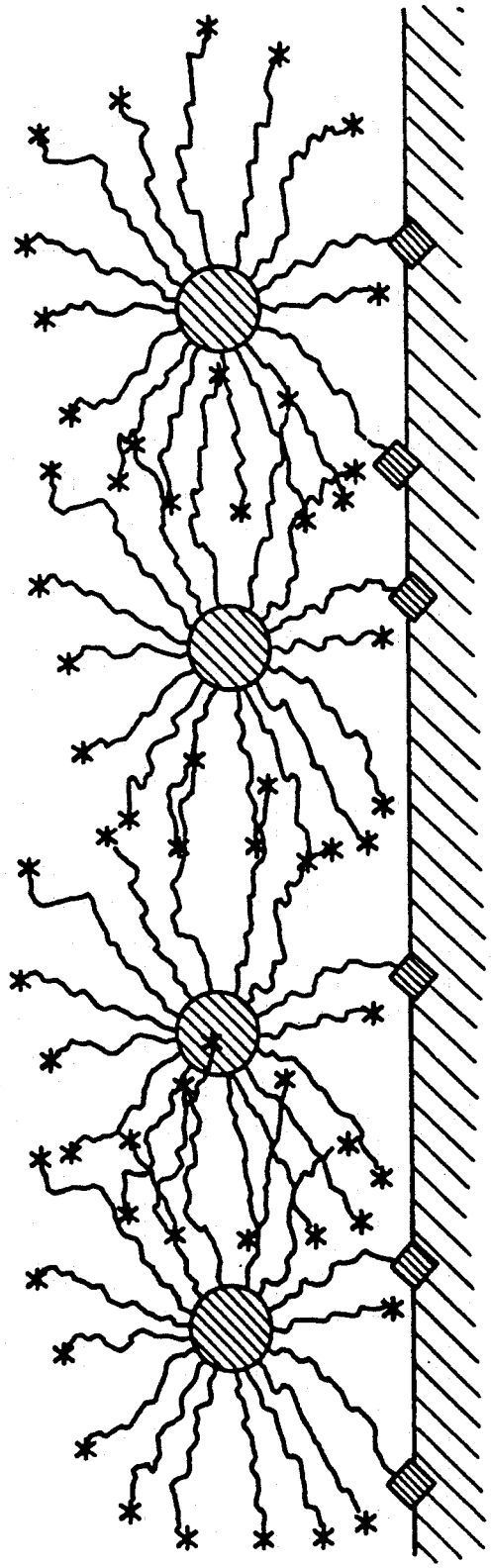
FIG. 3 shows several PEO star molecules (Type I) covalently attached to a support surface by tresylated hydroxyl groups.

This process is further described below by way of illustration. For example, a Cellophane TM (cellulose containing plasticizers) containing support is placed in a bath of tetrahydrofuran and tresyl chloride. The hydroxyl groups on the surface of the Cellophane TM are then tresylated. Once tresylated, the Cellophane TM is aminated in a water solution of mercaptoethanol amine (pH 10) which results in binding the group —SCH$_2$CH$_2$NH$_2$ to the activated hydroxyl groups. Likewise, star molecules are tresylated and then placed into an aqueous buffer (pH 10) containing the aminated Cellophane TM. After a period of time (approx. 1 hr), the Cellophane TM is removed from the solution and rinsed to wash off any unbound star molecules. The star molecules become bound to the amino group via the tresylated hydroxyls. FIG. 3 shows several PEO star molecules immobilized on a support surface. The attachment results from the reaction of amino groups on the support surface with tresylated hydroxyls on the star molecules.

Figure 4:
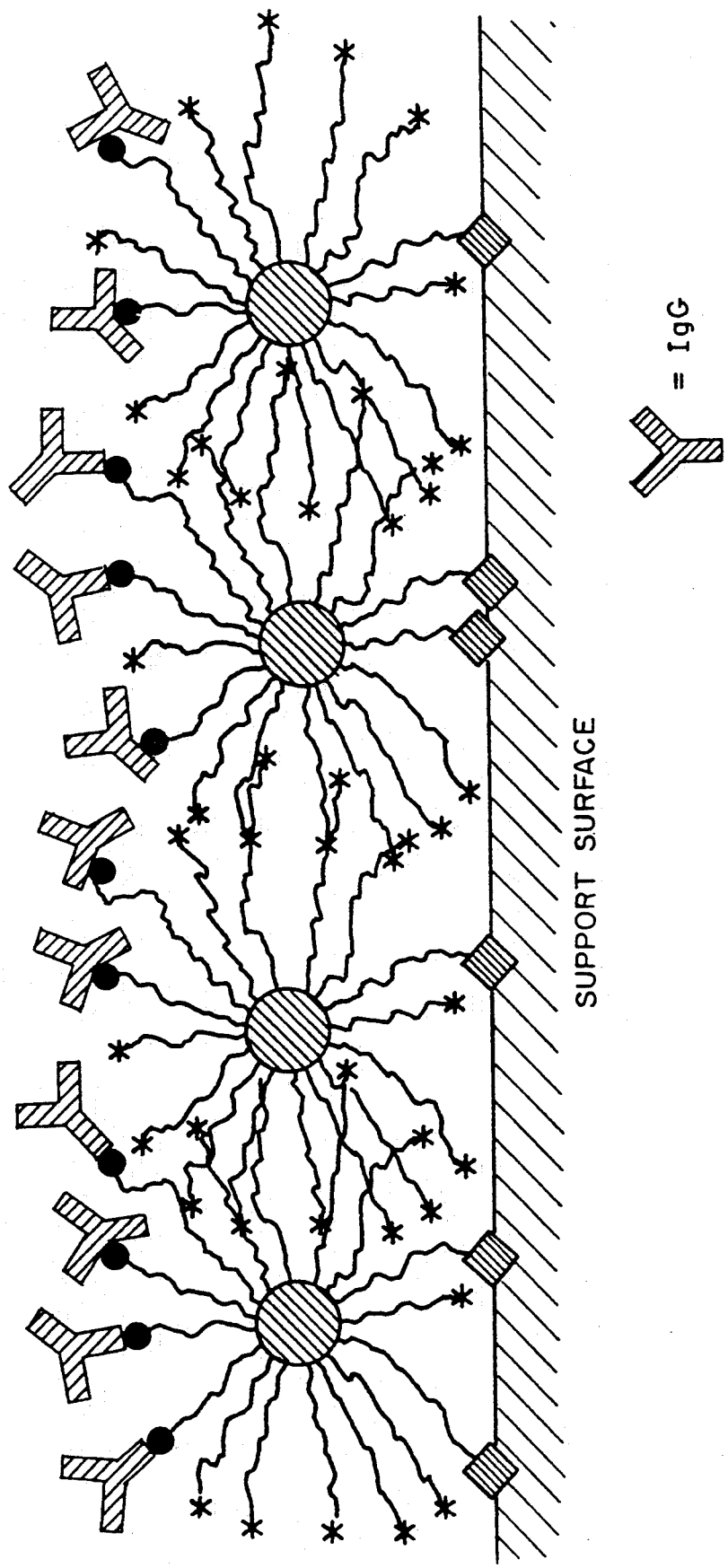
FIG. 4 illustrates the attachment of a biopolymer (IgG) to the surface of immobilized PEO star molecules.

The star molecule hydrogels can be covalently bonded onto an appropriate support surface using the method previously described to thereby protect the support from recognition by bipolymers. A monolayer coating of PEO star molecules can be accomplished by attaching one or more PEO arms to the support. The remaining arms remain available for attaching biopolymers or affinity ligands. The PEO-coated support surface can then be exposed to a biopolymer having amino or thiol groups which can couple to available tresylated hydroxyl groups. These available groups function as molecular leashes or tethers for the bipolymer. For example, anti-Protein C antibody can be attached to the star molecules and will be selective for its antigen, Protein C. The PEO monolayer prevents adsorption of the biopolymers onto the support surface and can thereby reduce or eliminate non-specific binding of undesired bipolymers. FIG. 4 demonstrates the use of star molecules for attaching affinity ligands, such as Immunoglobulin G. The symbol ◆ represents a covalent linkage between a PEO arm and an amino group on the support: ● represents a covalent linkage between a PEO arm and an amino or thiol group on IgG; ★ represents an endcapped previously tresylated hydroxyl (e.g., by treatment with mercaptoethanol).

Due to the number of available PEO arms which can accommodate ligands, the hydrogels of this invention can be used to continuously separate, purify and concentrate therapeutic proteins. Processing of the proteins will require cycles of coupling and decoupling of the ligate to affinity ligands bound to the stars.

The affinity surface can be of any geometric shape, such as particles packed in beds, freely moving particles and porous membranes. The hydrogels can be coated onto silica particles. In this case, polyethylene oxide is physically absorbed to the silica surface but cannot be covalently bound unless the silica has been previously modified. Nonetheless, the polyethylene oxide hydrogel forms a shell covering the particle and it thus cannot escape. The hydrogels can also be deposited into pores of ultrahigh molecular weight, high density polyethylene such as Porex TM (Auburn, Ga.), on the surface of Goretex TM e-PTFE (expanded polytetrafluoroethylene) and Mylar TM film.

In most cases, once a PEO hydrogel is coated onto the affinity surface, the terminal hydroxyl groups are activated by tresylation. Preferably, this is accomplished by contacting the hydrogel with tresyl chloride dissolved in an organic solvent, such as dichloromethane. The tresylated PEO star molecules are then placed in buffered aqueous solution containing the affinity ligand which is to be bound. Examples of preferred ligands include antibodies and $F_{ab}$ fragments thereof, Protein A, active polysaccharides, heparin-$NH_2$, anti-Protein C IgG, and the $F_{ab}$ fragment of anti-Protein C IgG.

Following affinity bonding of a specific ligate to its bound ligand, the hydrogel-coated affinity support is washed to remove unbound proteins. Remaining bound proteins are then decoupled by changing the composition of the eluting buffer, for example by changing the ionic strength or the pH (e.g., to pH 10 or above) of the eluting buffer. For example, a 1 M NaCl decoupling solution can be used in the case of antithrombin III bound to heparin. The decoupling results in free ligate in the eluting buffer. The ligate can then be separated from the eluting buffer using known techniques, such as by diafiltration described by Herak and Merrill, *Biotech. Prog.* 5:9-17 (1989). Separated ligates can then be constructed using known techniques. Examples of some specific ligates include macromolecules, monoclonal antibodies, antigens, viruses and cells (e.g., blood platelets, white blood cells, endothelial cells and other non-blood cells).

In addition to bioseparations, the hydrogels made according to this invention are useful for a variety of biomedical applications, due to their non-thrombogenic properties and excellent mechanical durability. They are suitable for in vivo applications in which blood contact is required, including blood contacting implantable vascular prostheses, angioplastic stents, cardiovascular sutures, metabolic support catheters, angioplastic balloon catheters, artificial hearts and ventricular assist devices. The hydrogels may also be used for ex vivo devices, such as hemadialysis membranes and membranes for extra-corporeal oxygenators.

Additional chemical components can be incorporated into the star hydrogels depending upon the application. In some instances it may be advantageous to incorporate heparin into the hydrogel to further reduce thromogenicity. While heparin can be attached covalently to tresylated hydroxyls on the star molecules, it is also readily incorporated at high concentrations in the hydrogel by simply adding it to the solution of the star before irradiation. In this form it elutes into the blood flow over a significant period of time.

The invention will be further illustrated by the following Example.

EXEMPLIFICATION

Synthesis and Characterization of Various PEO Hydrogels

Linear PEO and various forms of star molecules having the physical properties described below were electron beam irradiated, at a dose rate of about 0.1 megarad per second, and with a 2 megarad dose per pass under the beam to form hydrogels. Radiation was delivered from a 3 MeV Van de Graaff generator (MIT High Voltage Research Laboratory).

Table 1 presents the apparent swelling ratio q at 25° C. (q=volume of hydrogel equilibrated in water/volume of original mixture irradiated) as a function of radiation dose D in megarad, and as a function of the star type. Two linear PEO samples are included for reference. The concentration of the solution as irradiated in every case was 10.1 wt/vol. % in MilliQ® water. From Table 1 is apparent that the swelling ratio q of hydrogels formed from star molecules is significantly less than for hydrogels from linear PEO types. Furthermore, the high styrene content Type II hydrogels (3103, 3229) exhibit virtually no swelling.

TABLE 1

| | Swelling Ratios q of 10 wt/vol. % Polymer/Water After Electron Beam Irradiation | | | | | | | |
|---|---|---|---|---|---|---|---|---|
| | mol. wt. total | % S | # arms | $M_{PEO}$ | $M_{PS}$ | D | q | [OH] μM |
| Linear PEO | | | | | | | | |
| Nominal | | | | | | 4 | 2.03 | 0.33 |
| 300,000 m.w. | | | | | | 6 | 1.92 | 0.35 |
| Nominal | | | | | | 4 | 2.8 | 0.71 |
| 100,000 m.w. | | | | | | 6 | 2.4 | 0.83 |
| Type I Stars (no styrene) | | | | | | | | |
| 3098 | 229,000 | | 43 | 5300 | | 4 | 1.3 | 14.6 |
| 3210 | 142,000 | | 40 | 3460 | | 4 | 1.4 | 20.0 |
| 3224 | 79,000 | | 8 | 10,000 | | 6 | 1.6 | 6.3 |
| Type II Stars | | | | | | | | |

TABLE 1-continued

Swelling Ratios q of 10 wt/vol. % Polymer/Water
After Electron Beam Irradiation

| | mol. wt. total | % S | # arms | $M_{PEO}$ | $M_{PS}$ | D | q | [OH] μM |
|---|---|---|---|---|---|---|---|---|
| 3103 | 190,000 | 20 | 16 | 8000 | 2000 | 4 | ~1.0 | 8.4 |
| 3229 | 257,000 | 30 | 25 | 6800 | 3200 | 4 | ~1.0 | 9.6 |
| 3385 | 371,000 | 2 | 30 | 12,000 | 520 | 4 | 1.7 | 4.7 |
| | | | | | | 6 | 1.6 | 5.7 |

D: dose in megarads
Total mol. wt. of stars by light scattering
q: Swelling Ratio
[OH]: g. equiv. per liter of gel swollen to equilibrium in water at 25° C.

From the results, the random cross-linking of star molecules cannot be expected to lead to networks like those produced from randomly cross-linked linear macromolecules, in which the functionality of the junction $\phi$ is necessarily 4. In contrast, the incorporation of stars implies incorporation of junctions of high functionality $\phi$, i.e., $\phi = \#$ arms. Further, the "junction" is in effect a high modulus poly DVB core, in Type I stars, and an even more complicated entity, i.e., poly DVB with short polystyrene arms, in Type II stars. Thus, the space occupied by the "junction", and the thermodynamically adverse junction-water interaction place the star hydrogel beyond the tenets of the Flory-Huggins theory of swelling of randomly cross-linked networks.

The last column in Table 1 shows the molar hydroxyl content of the gel at equilibrium in water [OH], calculated as: (mols OH/100 g. dry polymer)$q^{-1}$, wherein the first term is determined as (number of arms/total mol. wt.)·100. Each original solution at 10 wt/vol. % contains 100 g dry polymer per liter. The final wt/vol. % polymer in the gel at equilibrium with water is thus 10/q. This is very important if the star hydrogel is to be deployed as a model biomaterial to which bioactive species are to be grafted. It is desirable to have a high value of [OH] and a low swelling ratio q in order that the biomaterial remain approximately in the shape in which it was cast. Stars 3098 and 3210 as hydrogels provide examples.

In the hydrated state, i.e., in equilibrium with blood plasma, preliminary studies of platelet deposition indicate that the surface of star hydrogel is entirely PEO, that is, the poly DVB core is buried and inaccessible, because of the fact that the Star hydrogel acts as if it were a hydrogel of linear PEO. Crosslinking of these arms is random granting that all PEO arms have approximately the same molecular weight on a given star type as a consequence of the anionic polymerization route. Under an electron beam hydroxyl radicals created from water constitute the principal reagent and therefore the PEO rather than the poly DVB and PS experiences macroradical formation and subsequent coupling. To some degree scission of the arms must occur competitively with cross-linking under radiation. The terminal hydroxyl concentrations [OH] calculated in Table 1 do not take this into account.

Biocompatability

Hydrogels containing Type I Stars 3098 or Type II Stars 3385, described above, were examined for biocompatability.

Tubular specimens of hydrogel were prepared from 10 wt./vol. % solutions of star polymers 3098 and 3385 using 0.7 ml of solution centrifugally cast and irradiated under 6 megarads inside glass tubes of 10 cm length×9 mm lumen. These were tested in an ex vivo shunt model [indium 111 labeled platelets, baboon] with uncoated glass tubes as control. Over a period of 1 hour at a blood flow rate of 100 ml/min., there was no increase of indium count above background for the two hydrogel surfaces, whereas in glass control tubes (no coating) the count more than trebled over background.

Using similar techniques, glass tubes lined with 0.7 ml hydrogels formed from 10 wt./vol. % solutions of linear PEO of 100,000 and 300,000 mol. wt., respectively, under the same dose were prepared. Upon equilibration at 25° C. with pure water, the apparent swelling ratios (final volume:initial volume) were: 1.3, 1.3, 2.8 and 2.0 for Star 3098, Star 3385, PEO 100,000 and PEO 300,000 hydrogels, respectively. Values of 1.3 as compared to 2 or more mean that the star polymer based hydrogels when exposed to blood do not expand to such a degree as to compromise attachment to the surface on which they were cast. The lack of platelet uptake indicates that the star polymers in hydrogel form present a "pure" PEO surface to blood. As such, the DVB cores were shielded from access of plasma proteins by the PEO arms.

Equivalents

Those skilled in the art will recognize, or be able to ascertain, using no more than routine experimentation, many equivalents to the specific embodiments of the invention described herein. Such equivalents are intended to be encompassed by the following claims.

I claim:

1. A method of immobilizing polyethylene oxide star molecules to a support surface in the form of a hydrogel, comprising the steps of:
   a) providing a solution comprising polyethylene oxide star molecules consisting essentially of a plurality of hydroxy-terminated polyethylene oxide chains attached to a polymeric core, the star molecules being essentially non-adsorptive toward biomolecules and nonthrombogenic;
   b) depositing the solution onto a support surface; and
   c) reacting the hydroxy-terminated polyethylene oxide chains of the star molecules to thereby produce a hydrogel which is immobilized to the support surface.

2. The method of claim 1, wherein step (c) is performed by irradiating the solution to produce a hydrogel of crosslinked star molecules; wherein the solution is an aqueous solution.

3. The method of claim 2, wherein the aqueous solution is irradiated by electron beam radiation.

4. The method of claim 1, further comprising the step of providing tresylated star molecules in an aqueous solution at a pH of above about 10 prior to step (b); and wherein the support surface contains active functional groups for immobilizing the tresylated star molecules thereto.

5. The method of claim 4, wherein the functional groups are thiol, amino or both.

6. A method of immobilizing polyethylene oxide star molecules to a support surface in the form of a hydrogel, comprising the steps of:
   a) providing an aqueous solution comprising polyethylene oxide star molecules consisting essentially of a plurality of hydroxy-terminated polyethylene oxide chains attached to a divinyl benzene core, the star molecules being essentially non-adsorptive toward bimolecules and nonthrombogenic;
   b) depositing the aqueous solution onto a support surface; and
   c) irradiating the solution with electron radiation to sufficiently crosslink the polyethylene oxide chains to produce a hydrogel of crosslinked star molecules which is thereby immobilized to the support surface.

7. The method of claim 6, wherein the support surface is selected from the group consisting of in vivo blood contacting vascular prostheses, angioplastic stents, cardiovascular suture, metabolic support catheters, angioplastic balloon catheters, artificial hearts and ventricular assist devices.

8. The method of claim 6, wherein the support surface is selected from the group consisting of hemodialysis membranes and membranes for extracorporeal oxygenators.

9. A product produced by the method of claim 6.

10. A method of immobilizing polyethylene oxide star molecules to a support surface in the form of a hydrogel, comprising the steps of:
    a) exposing an organic solution comprising polyethylene oxide star molecules consisting essentially of a plurality of hydroxy-terminated polyethylene oxide chains attached to a divinyl benzene core to tresyl chloride to affix tresyl groups to the hydroxy termini;
    b) transferring the tresylated polyethylene oxide star molecules from the organic solvent to an aqueous solution;
    c) adjusting the pH of the aqueous solution to about 10 or above; and
    d) contacting the solution of step (c) with a support surface containing amino and/or thiol groups to covalently bind the tresylated star molecules, thereby immobilizing the tresylated star molecules in a dense layer to the support surface.

11. The method of claim 10, wherein the support surface is selected from the group consisting of particles, porous polymeric membranes, polymeric film, and biomedical devices.

12. The method of claim 10, wherein the support surface is selected from the group consisting of in vivo blood contacting vascular prostheses, angioplastic stents, cardiovascular suture, metabolic support catheters, angioplastic balloon catheters, artificial hearts, ventricular assist devices, hemodialysis membranes and membranes for extracorporeal oxygenators.

13. A product produced by the method of claim 8.

14. The method of claim 10, further comprising the steps of:
    e) washing the support surface to remove any non-bound star molecules, leaving the tresylated polyethylene oxide star molecules remaining bound thereto; and
    f) contacting the support surface of step (e) with an affinity ligand of interest having amino and/or thiol groups thereon, to covalently bind the ligand to the polyethylene oxide chains.

15. The method of claim 14, wherein the affinity ligand is selected from the group consisting of antibodies, Protein A, $F_{ab}$ fragments of antibodies and active polysaccharides.

16. The method of claim 15, wherein the active polysaccharide is heparin.

* * * * *